United States Patent [19]

Yue et al.

[11] Patent Number: 5,582,977
[45] Date of Patent: Dec. 10, 1996

[54] DIMERS OF UNSYMMETRICAL CYANINE DYES

[75] Inventors: Stephen T. Yue, Eugene; Iain D. Johnson, Springfield; Richard P. Haugland, Eugene, all of Oreg.

[73] Assignee: Molecular Probes, Inc., Eugene, Oreg.

[21] Appl. No.: 180,763

[22] Filed: Jan. 6, 1994

Related U.S. Application Data

[63] Continuation of Ser. No. 761,177, Sep. 16, 1991, abandoned.

[51] Int. Cl.⁶ .............. C12Q 1/68; G01N 33/52; C07H 21/02; C07H 21/04
[52] U.S. Cl. .............. 435/6; 435/40.5; 536/23.1; 546/165
[58] Field of Search .............. 435/968, 6, 7.1, 435/34, 40.5; 536/23.1; 546/152, 165, 176

[56] References Cited

U.S. PATENT DOCUMENTS

| | | | |
|---|---|---|---|
| 4,304,908 | 12/1981 | Frishberg et al. | 544/105 |
| 4,883,867 | 11/1989 | Lee | 536/25.4 |

OTHER PUBLICATIONS

Chemical Abstracts vol. 88, No. 6, Abstract No. 38936q.
Brooker, et al., J. Am. Chem. Soc. 64, 199 (1942).
Lee, et al., *Thiazole Orange: A New Dye for Reticulocyte Analysis*, Cytometry 7, 508 (1986).
Rye, et al., Nucleic Acids Research 19(2), 327 (1990).
Haugland, Molecular Probes Handbook of Fluorescent Probes and Research Chemicals Set 28 (1989).
Griffiths, Colour and Constitution of Organic Molecules, pp. 241 Academic Press (1976).
Ausubel, et al., Short Protocols in Molecular Biology, p. 359, John Wiley & Sons.

*Primary Examiner*—David Guzo
*Attorney, Agent, or Firm*—Allegra J. Helfenstein; Anton E. Skaugset

[57] ABSTRACT

The invention relates to dimers of unsymmetrical cyanine dyes, typically dimers of benzthiazole or benzoxazole derivatives, that exhibit enhanced fluorescence on binding with DNA or RNA, The dimers generally have the formula:

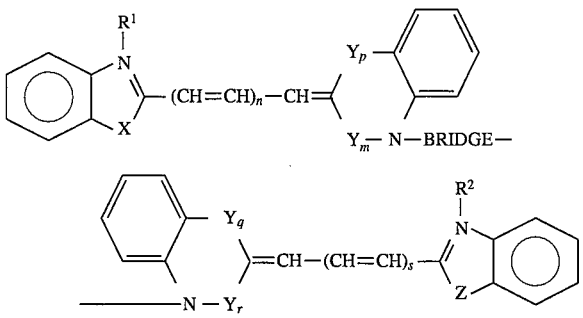

where
$R^1$ and $R^2$, which may be the same or different, are alkyl groups having 1–6 carbons;
X is O, S, or N—$R^3$, where $R^3$ is H or an alkyl group having 1–6 carbons;
Z is O, S, or N—$R^4$, where $R^4$ is H or an alkyl group having 1–6 carbons;
n and s, which may be the same or different, =0, 1, or 2;
Y is HC=CH; and
p, m, q, and r=0 or 1, such that p+m=1 and q+r=1; and
where -BRIDGE- has the general formula:

$$-(CH_2)_\alpha-[A^1-(CH_2)_\beta-]_I[A^2-(CH_2)_\gamma-]_{II}A^3-(CH_2)_\delta-$$

where α, β, γ, and δ, which may be the same or different, are integers greater than 1 and less than 5;
I and II, which may be the same or different, =0 or 1; and
$A^1$, $A^2$, and $A^3$, which may be the same or different, are independently O; S; $(CH_2)_\mu$ where μ=0 or 1; —(NR⁵)— where $R^5$ is H or an alkyl group having 1–6 carbons; or—($N^+R^6R^7$)— where $R^6$ and $R^7$, which may be the same or different, are independently hydrogen or an alkyl group having 1–6 carbons.

24 Claims, 5 Drawing Sheets

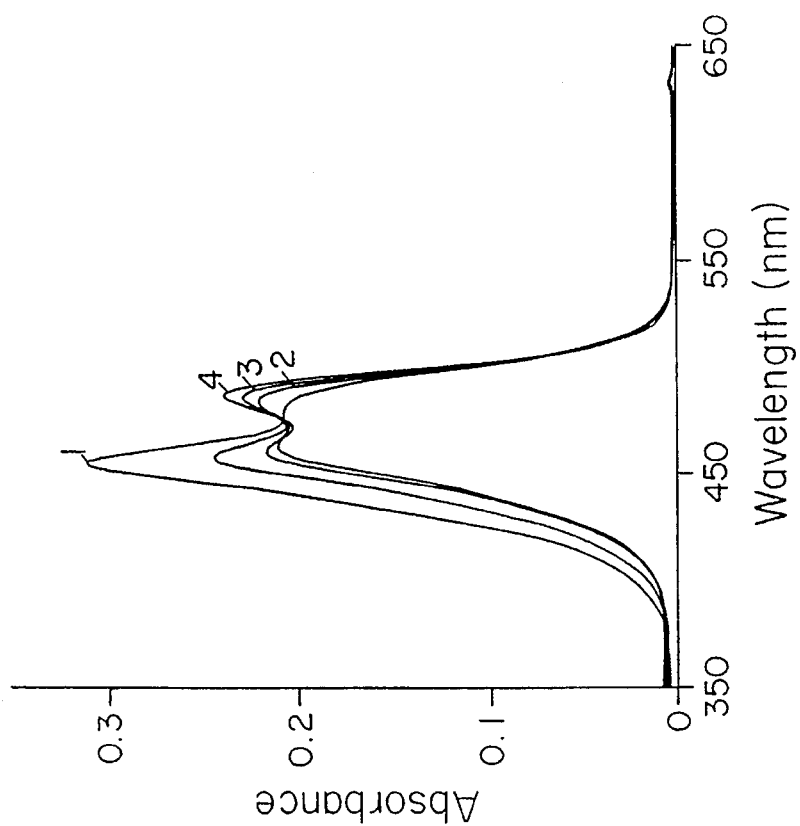
Figure 2
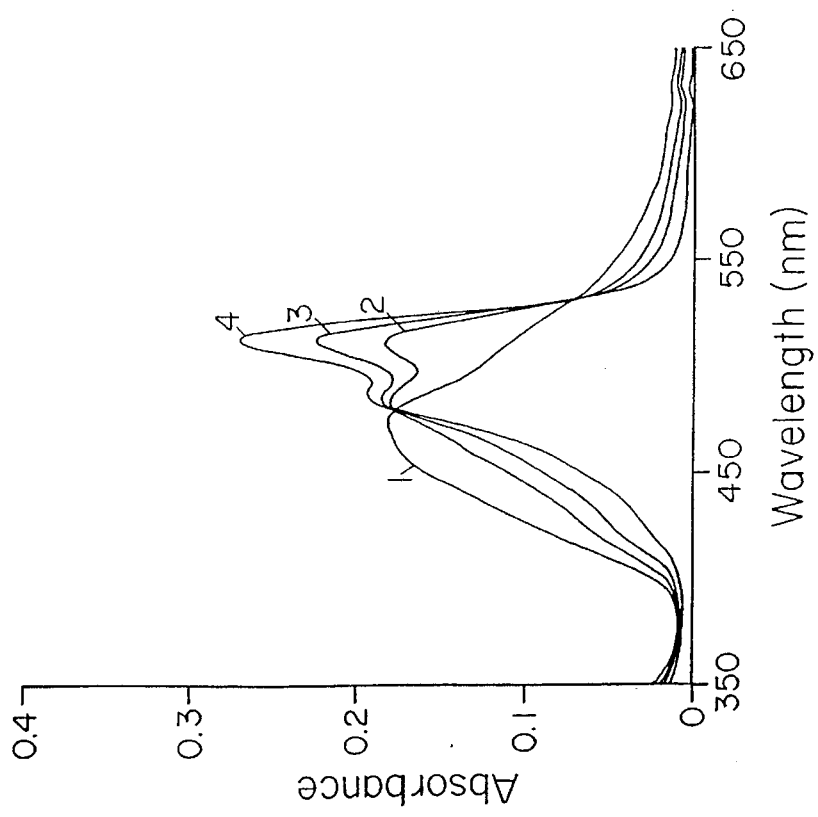
Figure 2A
Figure 2B

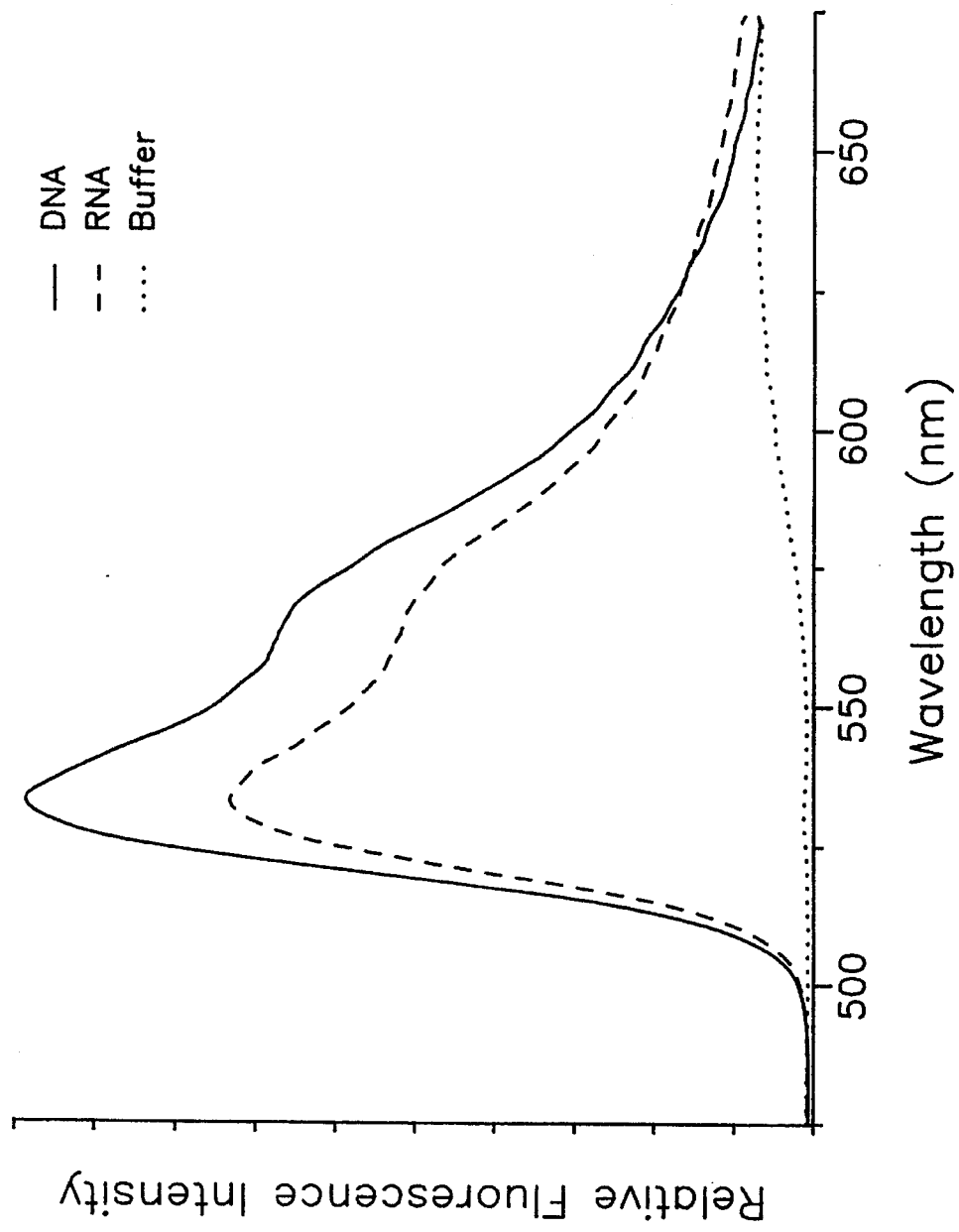

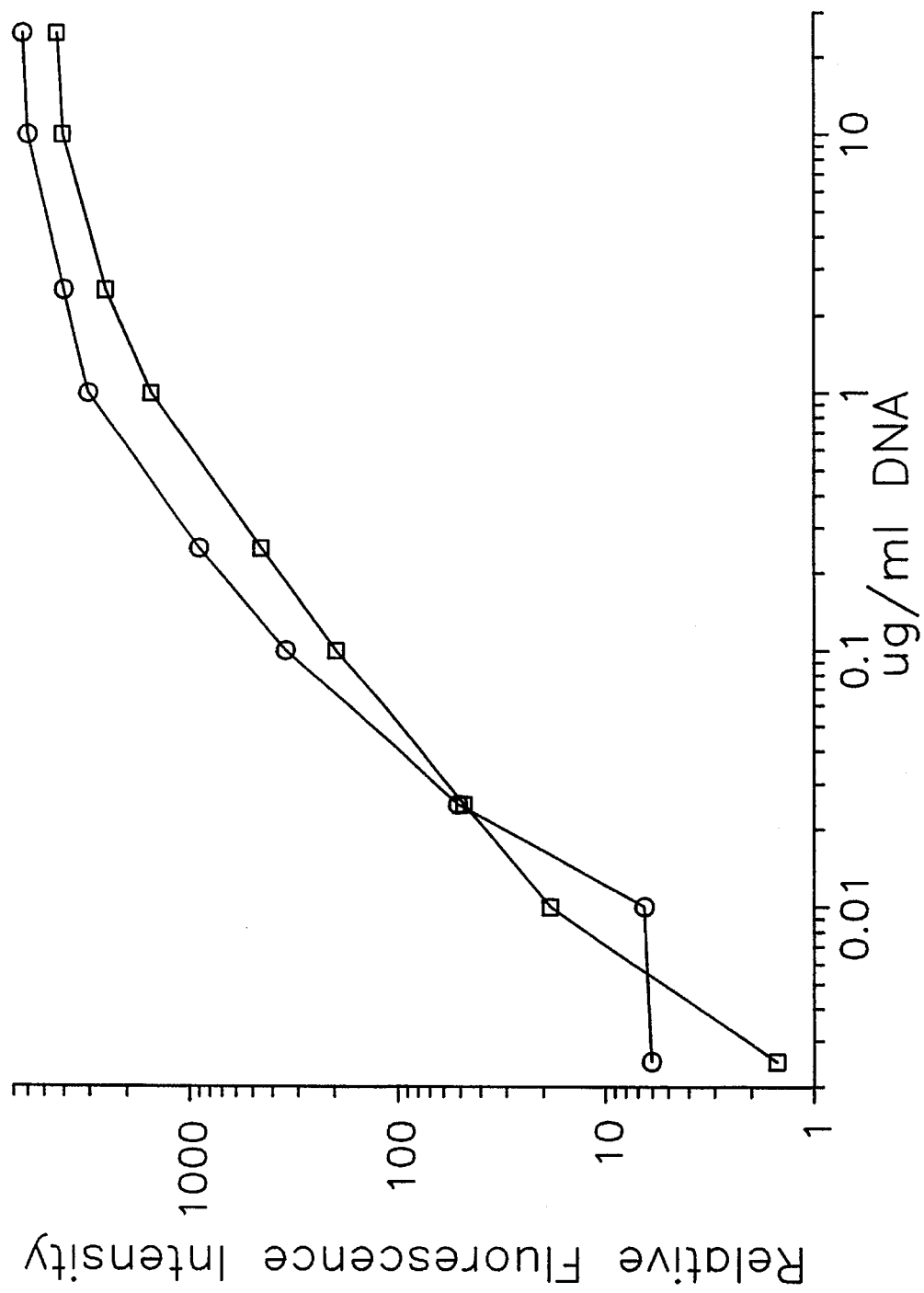

DIMERS OF UNSYMMETRICAL CYANINE DYES

This is a continuation of application Ser. No. 07/761,177, filed on Sep. 16, 1991 (now abandoned).

FIELD OF THE INVENTION

The invention relates to novel fluorescent dyes. In particular, the invention relates to dimers of unsymmetrical cyanine dyes used for nucleic acid staining.

BACKGROUND OF THE INVENTION

Fluorescent dyes have many uses and are known to be particularly suitable for biological applications in which the high detectability of fluorescence is desirable. By binding to a specific biological ingredient in a sample, a fluorescent dye can be used to indicate the presence or the quantity of the specific ingredient in a sample. A variety of fluorescent dyes are available for specific fluorescent staining and quantitation of DNA and RNA, and other applications involving nucleic acids.

Unsymmetrical cyanine dyes were described long before much was known about DNA by Brooker, et al., J. AM. CHEM. SOC. 64, 199 (1942). These dyes have since been found to be useful in fluorescent staining of DNA and RNA. The dye sold under the tradename Thiazole Orange has particular advantages in the quantitative analysis of immature blood cells or reticulocytes. U.S. Pat. No. 4,883,867 to Lee, et al. (1989) ('867 patent); Lee, et al., *Thiazole Orange: A New Dye for Reticulocyte Analysis*, CYTOMETRY 7, 508 (1986). As indicated in the '867 patent to Lee, et al., the dye used for this purpose must be able to penetrate the cell membrane.

The inventors have discovered that a composition that includes two suitably connected unsymmetrical cyanine dye units, i.e. a cyanine dye dimer, is a polar compound that is unable to readily penetrate cell membranes. Nevertheless, the composition discovered by inventors is highly useful as a stain for nucleic acids because it is sensitive to even small fragments of nucleic acid polymers not contained inside living cells, e.g. in cell extracts, as well as to nucleic acids in permeabilized cells. The dimer is neither anticipated nor obvious in view of Thiazole Orange or related compounds that are monomers.

Other dimer compounds that are known to bind to nucleic acids with a large fluorescence enhancement include variants of ethidium homodimer, acridine homodimers, acridine-ethidium heterodimer, and 7-hydropyridocarbazoles, see, e.g., Rye, et al., NUCLEIC ACIDS RESEARCH 19(2), 327 (1990); Haugland, MOLECULAR PROBES HANDBOOK OF FLUORESCENT PROBES AND RESEARCH CHEMICALS Set 28 (1989). Although the Rye, et al. reference mentions characteristics that influence the affinity and mode of binding dimers to DNA, the reference does not describe the compounds used in this invention. The novel dimer compounds described herein are not only different in structure from other dimer compounds but are also superior to other dimers and to Thiazole Orange in their sensitivity to nucleic acids.

A representative dimer is synthesized according to the procedure described in Examples 1 or 2. Where X is S, the compound is a dimer of a benzthiazole derivative. Where X is O, the compound is a dimer of a benzoxazole derivative.

FIG. 2. (Parts A–B) Absorption Spectra of Representative Compounds

FIG. 2A. Absorption spectra of a representative benzthiazole derivative dimer (Compound 1) ($4\times10^{-6}$M) in 10 mM Tris, 1 mM EDTA, 2M NaCl, pH 7.4 with addition of calf thymus DNA (Sigma Chem. Co. D-1501, Lot 118F-9525). DNA additions are: 1) none; 2) 11 µg/ml 3) 25 µg/ml and 4) 32 µg/ml. DNA concentrations are based on $A_{260}=1.0$ for 50 µg/ml DNA [Ausubel et al., SHORT PROTOCOLS IN MOLECULAR BIOLOGY, pp 359, John Wiley and Sons].

Figure 1:
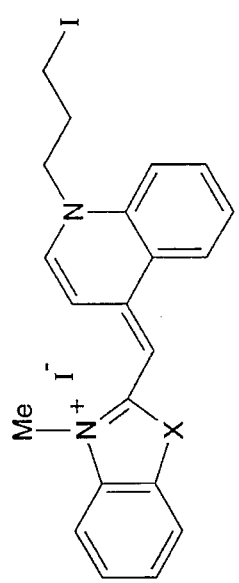
FIG. 1. Synthesis Pathway of a Representative Dimer from Intermediates
Figure 1:
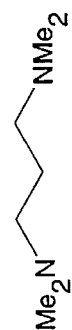
Figure 1:
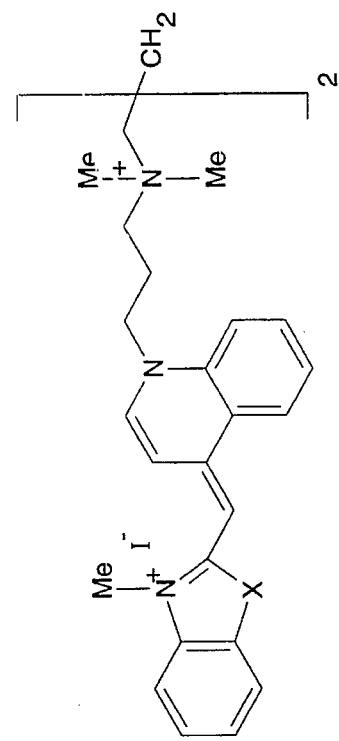

FIG. 2B. Absorption spectra of a representative benzoxazole derivative dimer (Compound 2) ($4\times10^{-6}$M) in 10 mM Tris, 1 mM EDTA, 2M NaCl, pH 7.4 with addition of calf thymus DNA (Sigma Chem. Co. D-1501, as FIG. 1). DNA additions are: 1) none; 2) 11 µg/ml 3) 25 µg/ml and 4) 32 µg/ml as in FIG. 1.

FIG. 3 (Parts A–B). Fluorescence Spectra of Representative Compounds

FIG. 3A. Fluorescence spectra of a representative benzthiazole derivative dimer (Compound 1) (1.0 µM) in 10 mM Tris, 1 mM EDTA, 2.0M NaCl, pH 7.4, showing effect of addition of DNA and RNA. Nucleic acid concentrations were: DNA (Calf Thymus DNA, Sigma Chemical Co. Product D-1501)=15.4 µg/ml and RNA (Calf Liver RNA, Sigma Chemical Co. Product R-7250)=18.6 µg/ml. Nucleic acid concentrations were calculated on the basis of $A_{260}$ nm=1.0=50 µg/ml double stranded DNA or 40 µg/ml single stranded RNA. Fluorescence spectra were recorded on an SLM Instruments SPF 500C spectrofluorometer with excitation at 450 nm. Fluorescence maximum in presence of DNA or RNA is 533 nm (±1 nm). Essentially similar nucleic acid induced fluorescence enhancement was observed (data not shown) in a low salt (50 mM NaCl) buffer with the exception that the weak long wavelength emission (maximum 645 nm) of the free dye was absent.

Figure 3B:
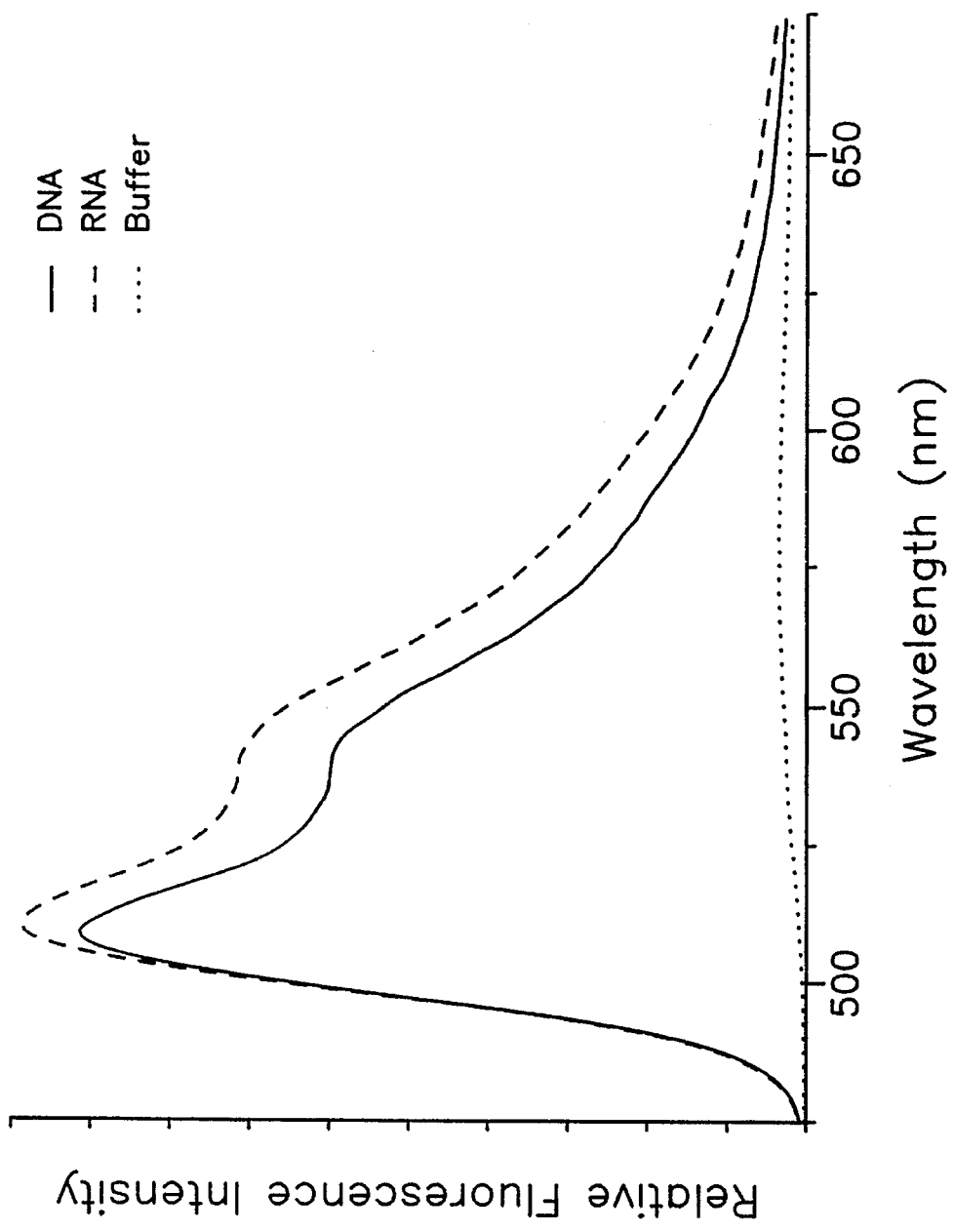

FIG. 3B. Effect of DNA and RNA on fluorescence spectra of a representative benzoxazole derivative dimer (Compound 2). All experimental conditions are the same as those used in the experiment shown in FIG. 3A. Fluorescence maximum in the presence of DNA or RNA is 509 nm (±1 nm).

FIG. 4. Titration of DNA.

DNA titrations of a representative benzthiazole derivative dimer (Compound 1) (□) and a representative benzoxazole derivative dimer (Compound 2) (○) in 10 mM Tris, 1 mM EDTA, 50 mM NaCl pH 7.4. The procedure of Example 6 is followed. All data points represent averages of duplicate determinations from which a blank reading for the same concentration of dye in the absence of DNA has been subtracted. The lowest detectable level of DNA in these measurements is 0.01 µg/ml which corresponds to 2 ng of DNA in the 200 µl analytical volume.

SUMMARY OF THE INVENTION AND DESCRIPTION OF PREFERRED EMBODIMENTS

The dyes used for the invention are dimers of unsymmetrical cyanine dye units. The dye units are linked by a bridge between the cyanine dye units. The two dye units, which may be the same or different, may be bridged symmetrically or asymmetrically. The novel dimers generally have the formula:

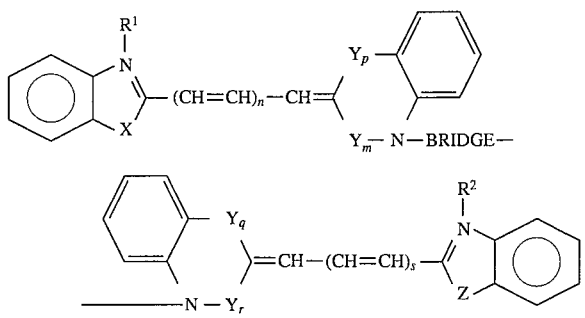

$R^1$ and $R^2$, which may be the same or different, are alkyl groups having 1–6 carbons. Preferably $R^1$ and $R^2$ have 1–3 carbons.

X is O, S, or N—$R^3$, where $R^3$ is H or an alkyl group having 1–6 carbons. Z, which may be the same as X or different, is O, S, or N—$R^4$, where $R^4$ is H or an alkyl group having 1–6 carbons. Preferably, X and Z are O or S. One embodiment of the invention is a dimer of benzoxazole analogs, where both X and Z are oxygen. Another embodiment of the invention is a dimer of benzthiazole analogs where both X and Z are sulfur.

The subscripts n and s, which determine the length of each dye unit, =0, 1, or 2. The dye units that form the dimer may be the same length or different. Changing the length of the dye units by increasing n or s or both will affect the spectral properties of the dye units and of the dimer.

Y is HC=CH, the position of which is indicated by the subscripts p, m, q, and r, which=0 or 1. When p=1, m=0 and vice versa. When q=1, r=0, and vice versa. When p and q equal 1, and n and s equal 0, and X and Z are sulfur, the compound is a dimeric analog of Thiazole Orange.

The BRIDGE linking the two dye units, which may be the same or different, is an aliphatic chain containing a backbone of 4–19 carbon atoms. The carbon backbone may be interspersed at one or more intervals with a non-carbon backbone atom ("heteroatom"). The heteroatoms, which may be the same or different are N, O, or S. Nitrogen is the preferred heteroatom. The nitrogen heteroatom may be substituted with one or more alkyl substituents having 1–6 carbon atoms, which alkyl substituents may be the same or different.

BRIDGE has the general formula:

$$—(CH_2)_\alpha—[A^1—(CH_2)_\beta—]_I[A^2—(CH_2)_\gamma—]_{II}A^3—(CH_2)_\delta—$$

The subscripts $\alpha$, $\beta$, $\gamma$, and $\delta$, which may be the same or different, indicate the size of the alkyl units, which contain from 2–4 carbon atoms each. The subscripts I and II, which may be the same or different, =0 or 1, indicating the presence or absence of that unit.

$A^1$, $A^2$, and $A^3$ may be the same or different. $A^1$ is an additional alkyl group $(CH_2)_\mu$, where $\mu=0$ or 1. Alternatively, $A^1$ is a heteroatom O or S, or a substituted or unsubstituted nitrogen heteroatom —$(NR^5)$— where $R^5$ is H or an alkyl group having 1–6 carbons, or —$(N^+R^6R^7)$— where $R^6$ and $R^7$, which may be the same or different, are independently hydrogen or an alkyl group having 1–6 carbons. Likewise, $A^2$ and $A^3$, which may be the same as or different from $A^1$ and each other, are independently $(CH_2)_\mu$ where $\mu=0$ or 1; O; S; —$(NR^5)$— where $R^5$ is H or an alkyl group having 1–6 carbons; or —$(N^+R^6R^7)$— where $R^6$ and $R^7$, which may be the same or different, are independently hydrogen or an alkyl group having 1–6 carbons. In a preferred embodiment, $A^1$ and $A^3$ are present as —$(N^+R^6R^7)$—. More preferably, $R^6$ and $R^7$ are methyl groups and II=0, eliminating the presence of $A^2$.

The spectral properties of the novel dimer compounds are similar to but different from those of known cyanine dyes. The novel dimer dyes (unbound) exhibit a strong absorption peak in the range of from about 400 nm to about 550 nm, however the dimers do not provide a detectable excitation or emission peak in the unbound state. Upon binding with DNA or RNA however, the optical properties of the dimers change dramatically. In particular, the absorption curve shifts to a longer wavelength, and the dye now exhibits strong fluorescence. The dimers of benzthiazole derivatives, combined with nucleic acid polymers, have an excitation maximum at about 510 nm and an emission maximum at about 530 nm, giving a Stokes shift of about 20 nm. The dimers of benzoxazole derivatives, combined with nucleic acid polymers, have an excitation maximum at about 490 nm and an emission maximum at about 510 nm, also giving a Stokes shift of about 20 nm (Table 1). It is worth noting that the argon ion laser, a high power source for fluorescence excitation, has principle output lines at 514 nm and 488 nm, which coincide closely with the excitation maxima of the novel dimers.

TABLE 1

Absorption and Fluorescence Maxima of Representative Benzthiazole (Compound 1) and Benzoxazole (Compound 2) Dimers.

| | Buffer[1] | Buffer + DNA[2] | Methanol |
|---|---|---|---|
| Compound 1 | | | |
| $\lambda_A$[3] | 475 | 513.2 | 507 |
| $\lambda_F$[4] | NF[5] | 533 | NF |
| Compound 2 | | | |
| $\lambda_A$ | 456 | 488 | 482 |
| $\lambda_F$ | NF | 509 | NF |

[1] 10 mM Tris, 2M NaCl, 1 mM EDTA: pH 7.4
[2] Between 15 and 35 mg/ml calf thymus DNA in the same buffer.
[3] $\lambda_A$ — wavelength of absorption maximum
[4] $\lambda_F$ — wavelength of fluorescence maximum
[5] NF — not sufficiently fluorescent for accurate determination As is well known for cyanine dyes, [Griffiths, COLOUR AND CONSTITUTION OF ORGANIC MOLECULES, pp. 241 Academic Press (1976)], increasing the length of the polymethine bridge between the heterocyclic terminal groups results in a shift of the absorption spectrum to longer wavelengths.

The fluorescence of the dimers bound to DNA or RNA is enhanced typically about 1000 fold, sometimes as much as 5000 fold, depending on the amount of nucleic acid present in the sample. (See, e.g., FIG. 4). This significant increase in fluorescence intensity eliminates the problem of background fluorescence due to unbound dye. The fluorescence intensity of the nucleic acid-dimer complex is proportional to the amount of nucleic acid in the sample (Example 6; FIG. 4).

Because the dimer compounds do not readily cross the cell membrane of a healthy cell, the detection of fluorescence in a sample of whole cells can be used as an indication of the viability of cells in the sample. Cell death or toxicity usually results in loss of cell membrane integrity. Thus, the fluorescence of single cells is an indicator that the cell membrane of such cells is not functioning normally, i.e. the fluorescent cells are not viable cells (Example 7).

EXAMPLE 1

PREPARATION OF A REPRESENTATIVE DIMER OF A BENZTHIAZOLE DERIVATIVE (Compound 1)

The following compound is prepared:

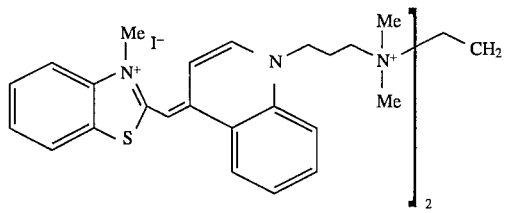

A mixture of 0.72 g of a 1'-(3'-iodopropyl)-3-methyl-thia-4'-cyanine iodide precursor (prepared according to methods known in the art e.g. Brooker, et al. J. AM. CHEM. SOC. 64, 199 (1942)), and 69 mg of N,N,N'N'-tetramethylpropanediamine in 5 mL of DMF is heated at 130° C. for one hour. After the reaction mixture cools down to room temperature, 40 mL of MeOH is added and stored at −20° C. overnight. The red solid is filtered and recrystallized from DMF/MeOH again to yield the pure product Compound 1.

EXAMPLE 2

PREPARATION OF A REPRESENTATIVE DIMER OF A BENZOXAZOLE DERIVATIVE (Compound 2)

The following compound is prepared:

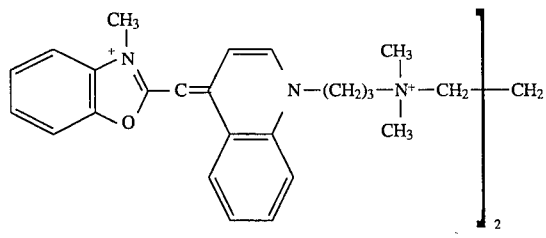

The appropriate benzoxazole derivative dimer precursors are prepared according to Brooker, et al. J. AM. CHEM. SOC. 64, 199 (1942) and is dimerized according to the procedure of Example 1.

EXAMPLE 3

PREPARATION OF A REPRESENTATIVE DIMER WITH INCREASED ABSORPTION WAVELENGTH (Compound 3)

A dimer of the following compound is prepared:

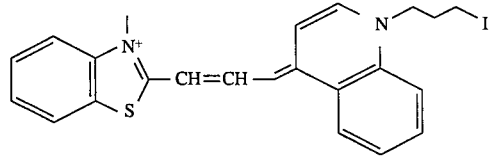

The monomer precursor is prepared from 2-(2-acetanilidovinyl)-3-methyl-benzothiazolium tosylate according to Brooker, et al. J. AM. CHEM. SOC. 64, 199 (1942) and is dimerized according to the procedure of Example 1.

EXAMPLE 4

PREPARATION OF A REPRESENTATIVE DIMER CONNECTED AT THE 2 POSITION OF THE QUINOLINE INSTEAD OF THE 4 POSITION (Compound 4)

The following compound is prepared:

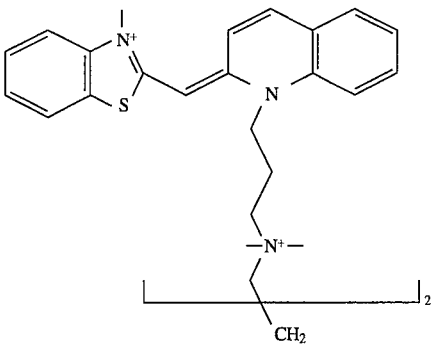

The precursor 1'-(3'-iodopropyl)-3-methylthio-2'-cyanine iodide is prepared according to the method of Brooker, et al., J. AM. CHEM. SOC. 64, 199 (1942) and dimerized as above.

EXAMPLE 5

PREPARATION OF A REPRESENTATIVE DIMER WITH AN UNSUBSTITUTED ALKYL BRIDGING GROUP (Compound 5)

The following compound is prepared:

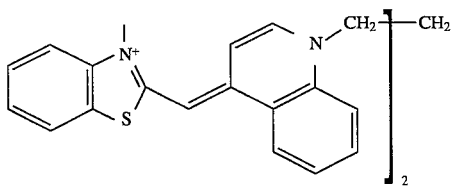

The compound is prepared from bi-(1'-(4-methylquinolinium)-1,3-propane dibromide and 2 equivalents of 2-methylthio-3-methylbenzothiazolium p-toluenesulfonate according to the method of Brooker, et al., J. AM. CHEM. SOC. 64, 199 (1942). The dibromide is obtained by refluxing 4.5 g of lepidine and 3 g of 1,3-dibromopropane in 4 ml of DMF for 6 hours. The solution is cooled to room temperature and 150 ml of ether is added to force out the product.

EXAMPLE 6

DNA TITRATIONS OF REPRESENTATIVE COMPOUNDS

A benzthiazole derivative dimer or a benzoxazole derivative dimer is prepared according to procedures described above. The dye concentration in buffer (10 mM Tris, 1 mM EDTA, 50 mM NaCl pH 7.4) is 1 μM. DNA (Calf Thymus DNA, Sigma Chemical Co. Product D-1501) is diluted from a 250 μg/ml stock solution (based on $A_{260\ nm}$=1.0=50 μg/ml). Fluorescence measurements are carried out on a Millipore Cytofluor 2300 microtiter plate reader using excitation at 485 nm (bandpass 20 nm) and emission detection at 530 nm (bandpass 25 nm). Fluorescence intensity is plotted against DNA concentration (FIG. 4).

EXAMPLE 7

QUANTITATIVE FLUORIMETRIC DETERMINATION OF DEAD CELLS

Cell line:

P3x63Ag8.653 (IgG, non-secreting mouse myeloma) from a BALB/c mouse. Medium for propagation: Dulbecco's modified Eagle's medium with 10% calf serum, 1% HEPES Buffer solution, 1% L-Glutamine, and 0.5% Gentamicin.

Procedure:

Allow the cells to propagate for 3 to 4 days. Wash the cells 2 times in phosphate buffered saline (PBS) and centrifuge at 700 rpm for 10 minutes. Resuspend in PBS. Count the cells by trypan blue exclusion using a hemocytometer. Determine viability and adjust the cell concentration to $1.2\times10^6$ cells/ml. Divide the cells into two populations. Kill one population, for example by heating to 60° C. for 15 minutes. Readjust the cell concentration to 600,000 cells/ml. Aliquot a known numbers of cells into a 96-well microtiter plate. Add PBS to the wells so that the volume is 200 µl. Add 100 µl of 6 µM of the dimeric dye to each sample well so that the final concentration of dye is 2 µM. Read the fluorescence versus cell number on a fluorescence microtiter plate reader (for example, Millipore Cytofluor 2300) using a suitable combination of excitation and emission filters. For compounds 1 and 2 excitation at 485 nm and emission detection at 530 nm is suitable. The linear proportionality of fluorescence signal to number of dead cells may be used to quantitatively assess cell viability. It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula:

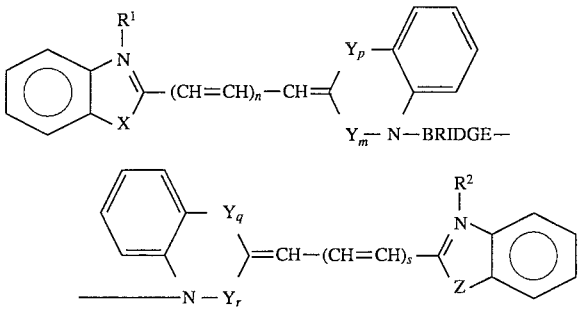

where $R^1$ and $R^2$, which may be the same or different, are alkyl groups having 1–6 carbons;

X is O, S, or N—$R^3$, where $R^3$ is H or an alkyl group having 1–6 carbons;

Z is O, S, or N—$R^4$, where $R^4$ is H or an alkyl group having 1–6 carbons;

n and s, which may be the same or different, =0, 1, or 2;

Y is HC=CH; and p, m, q, and r=0 or 1, such that p+m=1 and q+r=1; and where -BRIDGE- has the general formula:

$$-(CH_2)_\alpha-[A^1-(CH_2)_\beta-]_I[A^2-(CH_2)_\gamma-]_{II}A^3-(CH_2)_\delta-$$

where α, β, γ, and δ, which may be the same or different, are integers greater than 1 and less than 5;

I and II, which may be the same or different, =0 or 1;

$A^1$ and $A^2$, which may be the same or different, are independently O; S; $(CH_2)_\mu$ where µ=0 or 1; —($NR^5$)— where $R^5$ is H or an alkyl group having 1–6 carbons; or —($N^+R^6R^7$)— where $R^6$ and $R^7$, which may be the same or different, are independently hydrogen or an alkyl group having 1–6 carbons, and $A^3$ is S; $(CH_2)_\mu$ where µ=0 or 1; —($NR^5$)— where $R^5$ is H or an alkyl group having 1–6 carbons; or —($N^+R^6R^7$)— where $R^6$ and $R^7$, which may be the same or different, are independently hydrogen or an alkyl group having 1–6 carbons.

2. A compound, as claimed in claim 1, where $A^1$, $A^2$ and $A^3$, which may be the same or different, are independently $(CH_2)_\mu$, —($NR^5$)—, or —$N^+R^6R^7$)—.

3. A compound, as claimed in claim 1, where X and Z are the same; $R^1$ and $R^2$ are the same; n=s and m=r.

4. A compound, as claimed in claim 1, where m and r are each 1.

5. A compound, as claimed in claim 1, where X and Z, which may be the same or different, are O or S.

6. A compound, as claimed in claim 1, where n is not equal to s.

7. A compound, as claimed in claim 1, where $A^1$ and $A^3$, which may be the same or different, are independently —($NR^5$)— where $R^5$ is H or an alkyl group having 1–2 carbons; or —($N^+R^6R^7$)— where $R^6$ and $R^7$, which may be the same or different, are independently hydrogen or an alkyl group having 1–2 carbons; and II=0.

8. A compound, as claimed in claim 1, where $R^1$ and $R^2$, which may be the same or different, are alkyl groups having 1–2 carbons;

X and Z, which may be the same or different are O or S;

m and r=1;

in the BRIDGE formula

α, β, γ, and δ, which may be the same or different, are 2 or 3;

$A^1$, $A^2$, and $A^3$, which may be the same or different, are $(CH_2)_\mu$ where µ=0; —($NR^5$)— where $R^5$ is H or an alkyl group having 1–2 carbons; or —($N^+R^6R^7$)— where $R^6$ and $R^7$, which may be the same or different, are independently hydrogen or an alkyl group having 1–2 carbons.

9. A compound, as claimed in claim 3, where $R^1$ and $R^2$ are alkyl groups having 1–2 carbons;

X and Z are O or S;

m and r=1;

in the BRIDGE formula

α, β, γ, and δ, which may be the same or different, are 2 or 3;

$A^1$, $A^2$, and $A^3$, which may be the same or different, are $(CH_2)_\mu$ where µ=0; —($NR^5$)— where $R^5$ is H or an alkyl group having 1–2 carbons; or —($N^+R^6R^7$)— where $R^6$ and $R^7$, which may be the same or different, are independently hydrogen or an alkyl group having 1–2 carbons.

10. A fluorescent compound comprising a nucleic acid polymer bound to a dye of the general formula:

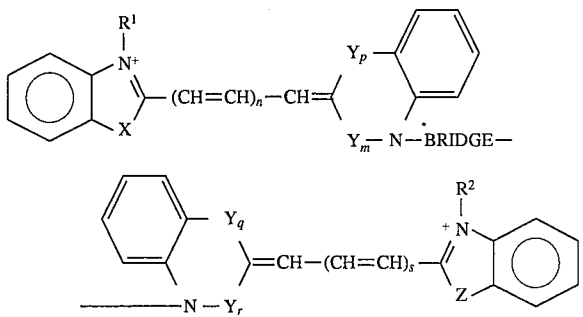

where

R$^1$ and R$^2$, which may be the same or different, are alkyl groups having 1–6 carbons;

X is O, S, or N—R$^3$, where R$^3$ is H or an alkyl group having 1–6 carbons;

Z is O, S, or N—R$^4$, where R$^4$ is H or an alkyl group having 1–6 carbons;

n and s, which may be the same or different, =0, 1, or 2;

Y is HC=CH; and p, m, q, and r=0 or 1, such that p+m=1 and q+r=1; and where -BRIDGE- has the general formula:

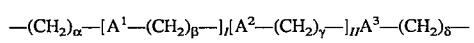

where α, β, γ, and δ, which may be the same or different, are integers greater than 1 and less than 5;

I and II, which may be the same or different, =0 or 1; and

A$^1$, A$^2$, and A$^3$, which may be the same or different, are independently O; S; (CH$_2$)$_\mu$ where μ=0 or 1; —(NR$^5$)— where R$^5$ is H or an alkyl group having 1–6 carbons; or —(N$^+$R$^6$R$^7$)— where R$^6$ and R$^7$, which may be the same or different, are independently hydrogen or an alkyl group having 1–6 carbons.

11. A compound, as claimed in claim 10, where A$^1$, A$^2$ and A$^3$, which may be the same or different, are independently (CH$_2$)$_\mu$, —(NR$^5$)—, or —(N$^+$R$^6$R$^7$)—.

12. A compound, as claimed in claim 10, where A$^1$ and A$^3$, which may be the same or different, are independently —(NR$^5$)— where R$^5$ is H or an alkyl group having 1–2 carbons; or —(N$^+$R$^6$R$^7$)— where R$^6$ and R$^7$, which may be the same or different, are independently hydrogen or an alkyl group having 1–2 carbons; and II=0.

13. A compound, as claimed in claim 10, where R$^1$ and R$^2$, which may be the same or different, are alkyl groups having 1–2 carbons;

X and Z, which may be the same or different are O or S;

m and r=1;

in the BRIDGE formula
α, β, γ, and δ, which may be the same or different, are 2 or 3;
A$^1$, A$^2$, and A$^3$, which may be the same or different, are (CH$_2$)$_\mu$ where μ=0; —(NR$^5$)— where R$^5$ is H or an alkyl group having 1–2 carbons; or —(N$^+$R$^6$R$^7$)— where R$^6$ and R$^7$, which may be the same or different, are independently hydrogen or an alkyl group having 1–2 carbons.

14. A compound, as claimed in claim 11, where X and Z are the same; R$^1$ and R$^2$ are the same; n=s and m=r.

15. A compound, as claimed in claim 11, where m and r are each 1; and where X and Z, which may be the same or different, are O or S.

16. A compound, as claimed in claim 11, where n is not equal to s.

17. A compound as claimed in claim 11, where the nucleic acid polymer is DNA.

18. A compound, as claimed in claim 11, where the nucleic acid polymer is RNA.

19. A compound, as claimed in claim 14, where R$^1$ and R$^2$ are alkyl groups having 1–2 carbons;

X and Z are O or S;

m and r=1;

in the BRIDGE formula
α, β, γ, and δ, which may be the same or different, are 2 or 3;
A$^1$, A$^2$, and A$^3$, which may be the same or different, are (CH$_2$)$_\mu$ where μ=0; —(NR$^5$)— where R$^5$ is H or an alkyl group having 1–2 carbons; or —(N$^+$R$^6$R$^7$)— where R$^6$ and R$^7$, which may be the same or different, are independently hydrogen or an alkyl group having 1–2 carbons.

20. A method of forming a fluorescent nucleic acid complex, comprising:

a) combining a sample thought to contain nucleic acid polymers with a dye of the general formula:

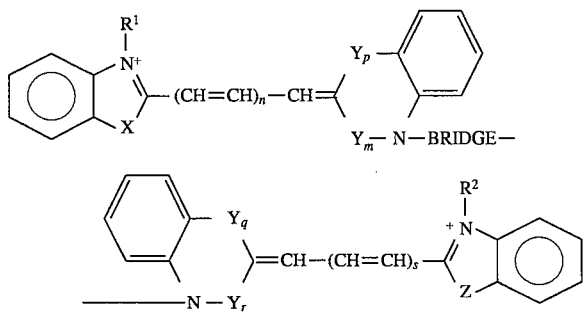

where

R$^1$ and R$^2$, which may be the same or different, are alkyl groups having 1–6 carbons;

X is O, S, or N—R$^3$, where R$^3$ is H or an alkyl group having 1–6 carbons;

Z is O, S, or N—R$^4$, where R$^4$ is H or an alkyl group having 1–6 carbons;

n and s, which may be the same or different, =0, 1, or 2;

Y is HC=CH; and p, m, q, and r=0 or 1, such that p+m=1 and q+r=1; and where -BRIDGE- has the general formula:

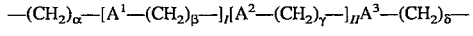

where α, β, γ, and δ, which may be the same or different, are integers greater than 1 and less than 5;

I and II, which may be the same or different, =0 or 1; and

A$^1$, A$^2$, and A$^3$, which may be the same or different, are independently O; S; (CH$_2$)$_\mu$ where μ=0 or 1; —(NR$^5$)— where R$^5$ is H or an alkyl group having 1–6 carbons; or —(N$^+$R$^6$R$^7$)— where R$^6$ and R$^7$, which may be the same or different, are independently hydrogen or an alkyl group having 1–6 carbons;

b) after the dye has been allowed to combine with any nucleic acid polymers in said sample, detecting fluorescence resulting from the dye combining with nucleic acid polymers.

21. A method, as in claim 20, wherein the nucleic acid polymers in the sample are contained in cells.

22. A method, as in claim 20, wherein the sample contains nucleic acid polymers in solution.

23. A method, as in claim 20, where $R^1$ and $R^2$, which may be the same or different, are alkyl groups having 1–2 carbons;

X and Z, which may be the same or different are O or S;

m and r=1;

in the BRIDGE formula

α, β, γ, and δ, which may be the same or different, are 2 or 3;

$A^1$, $A^2$, and $A^3$, which may be the same or different, are $(CH_2)_\mu$; —$(NR^5)$— where $R^5$ is H or an alkyl group having 1–2 carbons; or —$(N^+R^6R^7)$— where $R^6$ and $R^7$, which may be the same or different, are independently hydrogen or an alkyl group having 1–2 carbons.

24. A method, as in claim 21, wherein said fluorescence indicates loss of cellular membrane integrity.

* * * * *